United States Patent
Gerdes et al.

(10) Patent No.: US 10,029,067 B2
(45) Date of Patent: Jul. 24, 2018

(54) DEVICES, SYSTEMS AND METHODS FOR MONITORING BRAIN ACTIVITY AND FOR ENABLING BRAIN TO REBALANCE

(71) Applicant: Brain State Technologies, LLC, Scottsdale, AZ (US)

(72) Inventors: Lee Gerdes, Scottsdale, AZ (US); Peter Gerdes, Fountain Hills, AZ (US); Russell Loucks, Eagan, MN (US); Paul Hastings, Minneapolis, MN (US); Gillan Smith, Chandler, AZ (US); Sung Lee, Scottsdale, AZ (US)

(73) Assignee: Brain State Technologies, LLC, Scottsdale, AZ (US)

( * ) Notice: Subject to any disclaimer, the term of this patent is extended or adjusted under 35 U.S.C. 154(b) by 0 days.

(21) Appl. No.: 15/550,200

(22) PCT Filed: Aug. 15, 2016

(86) PCT No.: PCT/US2016/046970
§ 371 (c)(1),
(2) Date: Aug. 10, 2017

(87) PCT Pub. No.: WO2017/031028
PCT Pub. Date: Feb. 23, 2017

(65) Prior Publication Data
US 2018/0154104 A1    Jun. 7, 2018

Related U.S. Application Data

(60) Provisional application No. 62/207,233, filed on Aug. 19, 2015, provisional application No. 62/242,673, filed on Oct. 16, 2015.

(51) Int. Cl.
*A61M 21/00* (2006.01)
*A61B 5/048* (2006.01)
(Continued)

(52) U.S. Cl.
CPC ............. *A61M 21/00* (2013.01); *A61B 5/048* (2013.01); *A61B 5/04012* (2013.01);
(Continued)

(58) Field of Classification Search
CPC .... A61M 21/00; A61B 5/048; A61B 5/04012; A61B 5/0478; A61B 5/486; A61B 5/0482
(Continued)

(56) References Cited

U.S. PATENT DOCUMENTS 7,460,903 B2   12/2008   Pineda et al.
8,244,341 B2   8/2012    Hinrikus et al.
(Continued)

FOREIGN PATENT DOCUMENTS

WO        2017031028 A1     2/2017

OTHER PUBLICATIONS

Gerdes, Lee et al., HIRREM: a noninvasive, allostatic methodology for relaxation and auto-calibration of neural osciallations, Brain and Behavior, pp. 193-205 (2013).
(Continued)

*Primary Examiner* — John Lacyk
(74) *Attorney, Agent, or Firm* — Dorf & Nelson LLP; Scott D. Locke, Esq.

(57) ABSTRACT

Exposure to stressors may be associated with the production of asymmetry in brain waves and can significantly affect a person's overall degree of wellbeing and conversely, asymmetry may influence a person's experience of stress. Through devices and methods that simultaneously look for asymmetries and in real time, one can create real time variable sequences of acoustical stimuli, and then one can effectively and efficiently support the brain to balance its activity between corresponding right and left lobes without
(Continued)

one's mindful attention. Additionally various devices and methods can be used to identify condition states, including stress state conditions.

18 Claims, 3 Drawing Sheets

(51) Int. Cl.
*A61B 5/04* (2006.01)
*A61B 5/00* (2006.01)
*A61B 5/0478* (2006.01)

(52) U.S. Cl.
CPC .......... *A61B 5/0478* (2013.01); *A61B 5/6814* (2013.01); *A61B 5/7246* (2013.01); *A61M 2021/0027* (2013.01); *A61M 2205/3303* (2013.01); *A61M 2230/10* (2013.01)

(58) Field of Classification Search
USPC ..................................................... 600/26–28
See application file for complete search history.

(56) References Cited

U.S. PATENT DOCUMENTS

| | | |
|---|---|---|
| 8,249,699 B2 | 8/2012 | Gerdes |
| 9,345,418 B2 | 5/2016 | Alkire |
| 9,381,352 B2 | 7/2016 | Yun et al. |
| 9,399,126 B2 | 7/2016 | Pal et al. |
| 9,427,581 B2 | 8/2016 | Simon et al. |
| 9,433,773 B2 | 9/2016 | Chao et al. |
| 2007/0185533 A1 | 8/2007 | Gerdes |
| 2009/0281447 A1 | 11/2009 | Gerdes |
| 2012/0271377 A1 | 10/2012 | Hagedorn et al. |
| 2014/0058189 A1 | 2/2014 | Stubbeman |

OTHER PUBLICATIONS

Quraan, Maher, EEG Power Asymmetry and Functional Connectivity as a Marker of Treatment Effectiveness in DBS Surgery for Depression, Neuorpsychopharmacology (2014) 39, 1270-1281.

Lee, Sung et al., A bihemispheric autonomic model for traumatic stress effects on health and behavior, Frontiers in Psychology, vol. 5, Article 843, pp. 1-14 (Aug. 1, 2014).

Tegler, Charles H. et al., Rightward dominance in temporal high-frequency electrical asymmetry corresponds to higher resting heart rate and lower baroreflex sensitivity in a heterogeneous population, Brain and Behavior, pp. 1-7 (2015).

Gerdes, Lee et al., A groundwork for allostatic neuro-education, Frontiers in Psychology, Frontiers in Psychology, vol. 6, Article 1224 pp. 1-16 (Aug. 17, 2015).

Fortunato, John E. et al., Use of an allostatic neurotechnology by adolescents with postural orthostatic tachycardia syndrome (POTS) is associated with improvements in heart rate variability and changes in temporal lobe electrical activity, Exp. Brain Res., (2016) 234:791-798.

Strickland, Eliza, Brain-Zapping Gadgets Need Regulation, Say Scientists and (Some) Manufacturers (Aug. 31, 2016).

International Search Report and Written Opinion, PCT/US16/46970 (dated Oct. 28, 2016).

DEVICES, SYSTEMS AND METHODS FOR MONITORING BRAIN ACTIVITY AND FOR ENABLING BRAIN TO REBALANCE

CROSS-REFERENCE TO RELATED APPLICATIONS

This application is national stage application of PCT/US2016/046970, filed Aug. 15, 2016, which claims the benefit of the filing dates of U.S. provisional patent application Ser. No. 62/207,233, filed Aug. 19, 2015 and of U.S. provisional patent application Ser. No. 62/242,673, filed Oct. 16, 2015, the entire disclosures of which are incorporated by reference.

GOVERNMENT RIGHTS

This invention was made with government support under A14A-T009, which was awarded by the U.S. Army Research Office. The U.S. government may have certain rights in this invention.

FIELD OF THE INVENTION

The present invention relates to the field of monitoring and balancing brain waves.

BACKGROUND OF THE INVENTION

Many undesirable physiological states are correlated with changes in brain activity. These changes in brain activity create electromagnetic energy profiles that can be measured by devices such as electroencephalogram ("EEG") amplifiers and computers. Among the changes in brain activity that are known to be undesirable is an excess asymmetry between activity in the corresponding right and left regions of corresponding lobes of the brain.

One suggestion for restoring symmetry is presented in U.S. Pat. No. 8,249,699, Method of Affecting Balanced Brain Function with Relational Ambient Sound, issued Aug. 21, 2012 to Brain State Technologies, LLC. According to its teaching, due to the ability of the brain to associate sounds with brain waves and then change its own behavior, a subject is able to develop a relationship between the process of bringing his or her brain to a balanced state and an ambient sound, whereby the ambient sound adds a dimension for the brain to remember moving toward balance. As a result of this relationship, during times of imbalance, one may rebalance that subject's brain functioning.

The teachings of U.S. Pat. No. 8,249,699 illustrate in detail the phenomenon that persons of ordinary skill in the art will recognize as mirroring, which is distinct from the neuro-feedback teachings of operant conditioning. Strategies that rely on neuro-feedback, including those that rely on EEG biofeedback, have limitations with respect to both precision and speed. Furthermore, they require the mindful attention of the user, which refers to consciously trying to force the brain to do something rather than allowing an experience to simply relax the brain so that the brain can do something on its own terms.

The brain is a complex and active organ, and there remains a need for new and nonobvious technologies and methods for observing and analyzing brain activity and for using mirroring to balance brain activity without requiring the mindful attention of the user. Various embodiments of the present invention are directed to one or both of those needs.

SUMMARY OF THE INVENTION

Various embodiments of the present invention provide technologies and methods for one or both of detecting asymmetries in activity of corresponding lobes of the brain and balancing bi-hemispheric regions of the brain. In these embodiments, pairs of channels are used to measure brain electromagnetic energy by detecting changes in electric potentials. The measurements are translated from analog to digital and used to calculate brain rhythms. One may analyze these brain rhythms in order to determine when there are threshold asymmetries between corresponding lobes of the brain of a user of these technologies. When asymmetries are observed, one may use the data to do one or both of identifying condition states, e.g., stress states, and through brain mirroring technologies, reducing or eradicating the asymmetry. Through the use of the technologies of the present invention, a user's brain may be able to rebalance itself without requiring the attention or volition of the user of the invention.

According to a first embodiment, the present invention provides a system for measuring asymmetry of brain activity, wherein said system comprises: (a) a device, wherein the device is configured to rest on a user's head and said device comprises a set of channels, wherein the set of channels comprises (i) a first pair of corresponding lobe channels, wherein the first pair of corresponding lobe channels comprises a right first lobe channel and a left first lobe channel, wherein the right first lobe channel and the left first lobe channel are located on opposite halves of the device, and (ii) a second pair of corresponding lobe channels, wherein the second pair of corresponding lobe channels comprises a right second lobe channel and a left second lobe channel, wherein the right second lobe channel and the left second lobe channel are located on opposite halves of the device, wherein each channel is configured to measure electromagnetic energy in a region of a brain of a user and to generate a measurement of electromagnetic energy and wherein the first pair of corresponding lobe channels is configured to measure electromagnetic energy from a first lobe and the second pair of corresponding lobe channels is configured to measure electromagnetic energy from a second lobe, wherein the first lobe is not the same as the second lobe; (b) an asymmetry determination computer program product, wherein the asymmetry determination computer program product is stored in a tangible medium and when applied determines (and thus is designed to be capable of determining) whether during one or more time periods there is a threshold difference in energy between energy measured within any one or more of a first subrange of frequencies, a second subrange of frequencies, and a third subrange of frequencies from a right lobe channel and within a corresponding subrange of a corresponding left lobe channel, wherein the second subrange consists of frequencies greater than the frequencies in the first subrange and the second subrange consists of frequencies smaller than the frequencies in the third subrange; and (c) a central processing unit, wherein the central processing is configured to receive said measurements of electromagnetic activity from the device and to execute the asymmetry determination computer program product. Throughout this disclosure, systems and methods are described in which there are three subranges; however, the technologies of the present invention may be used to obtain finer resolution of brain activity and for example, be divided into 3-48 subranges, e.g., 11 subranges or 48 subranges with reach subrange corresponding to different sets of frequencies. By using a larger number of and smaller subranges one may be able to obtain a greater understanding of the characteristics of asymmetries when present.

According to a second embodiment, the present invention provides a method for identifying a condition state comprising: (a) measuring brain activity and creating a data message through a system of the present invention; (b) activating a computer protocol that correlates (and thus is capable of correlating) asymmetries in brain activity with a condition state, e.g., one or more stress states; (c) retrieving the identity of at least one condition state; and (d) generating an output in either or both of computer readable form and human readable form, wherein the output comprises information that corresponds to the at least one condition state. The computer protocol may, for example, access a local or remote database that associates asymmetry profiles with stress states or other condition states.

According to a third embodiment, the present invention provides a system for restoring symmetry in a brain comprising another system of the present invention disclosed herein, including but not limited to the system of the first embodiment described above, wherein the device of the system further comprises at least one speaker and the system further comprises: (a) a correlation algorithm, wherein the correlation algorithm correlates (or accesses a database that correlates and is thus capable of correlating) each of a plurality of frequencies from a set of brain wave frequencies with an acoustical stimulus such as a tone or musical note; and (b) a playback computer program product, wherein the playback computer program product is stored in a tangible medium and is configured (i) to be activated when there is material asymmetry in activity between the measurements from a subrange of frequencies of either the right first lobe channel and the left first lobe channel or the right second lobe channel and the left second lobe channel; (ii) to apply an algorithm that translates a plurality of dominant frequency brain waves from the second subrange of the lobe for which there is said material asymmetry into acoustical stimuli; and (iii) to control playing said acoustical stimuli through said at least one speaker, wherein said acoustical stimuli provide a real time mirror of said plurality of dominant frequency brain waves from the second subrange. In the system, the asymmetry determination computer program product may be further configured such that upon occurrence of a trigger event (e.g., a predetermined change in asymmetry level in any pair of subranges of corresponding lobes or at regular intervals), it dynamically switches the lobes from which the asymmetry determination computer program product obtains the dominant frequencies.

According to a fourth embodiment, the present invention provides a method for restoring brain symmetry comprising: (a) simultaneously measuring electromagnetic activity of a user's brain through a set of channels, wherein the set of channels comprises (or consists of or consists essentially of) (i) a first pair of corresponding lobe channels, wherein the first pair of corresponding lobe channels comprises a right first lobe channel and a left first lobe channel, wherein the right first lobe channel and the left first lobe channel are located on opposite halves of a device, and (ii) a second pair of corresponding lobe channels, wherein the second pair of corresponding lobe channels comprises a right second lobe channel and a left second lobe channel, wherein the right second lobe channel and the left second lobe channel are located on opposite halves of the device, wherein each channel is configured to measure electromagnetic energy in a region of a brain of a user and to generate a measurement of electromagnetic energy and wherein each pair of corresponding lobe channels is configured to measure electromagnetic energy in opposite hemispheres of a corresponding set of lobes; (b) activating an asymmetry determination computer program product, wherein the asymmetry determination computer program product is stored in a tangible medium and when applied determines whether there is a threshold difference in energy between energies measured within any one or more of a first subrange of frequencies, a second subrange of frequencies, and a third subrange of frequencies of corresponding lobe channels; (c) when there is a determination of a threshold difference in energy, activating a correlation algorithm, wherein for each of a plurality of frequencies from a set of dominant brain wave frequencies from the lobe for which there has been a determination of a threshold difference in energy, the correlation algorithm identifies an acoustical stimulus, e.g., a musical note or tone; (d) creating a variable sequence of acoustical stimuli by combining each acoustical stimulus identified in (c); and (e) playing said variable sequence of acoustical stimuli through a sound output device, wherein the set of channels and the sound output device are housed in a structure that is designed to rest on a user's head and wherein during step (e) said channels continue to measure electromagnetic activity and the asymmetry determination computer program product is further configured to switch the lobes dynamically from which the asymmetry determination computer program product obtains the dominant frequencies upon occurrence of a trigger event.

The variable sequence of acoustical stimuli may vary with respect to pitch and/or timing. A "variable sequence of acoustical stimuli" (which also may be referred to as a "varying sequence of acoustical stimuli") is a sequence of sounds that change over time; however, over time, the same sound may be repeated once or a plurality of times depending on the instructions of the relevant algorithm. Thus, although variable, it is not random and any given sequence may be unique. Additionally, the variable sequence of acoustical stimuli is played in real time while the channels continue to monitor for asymmetries and in some embodiments, the method further comprises dynamically switching the channels from which the dominant frequencies are used to create the varying sequence of acoustical stimuli. The switching may occur automatically upon a triggering event.

Various embodiments of the present invention may be used to measure asymmetry in brain activity and optionally to identify condition states, including but not limited to stress states. Additional various embodiments of the present invention may be used to restore (or to allow the brain itself to restore or to move toward restoration of) brain balance that may be compromised in association with a number of undesirable states, including but not limited to undesirable stress levels.

Through certain of these embodiments, the technologies disclosed herein support the brain to recover more optimal oscillatory dynamics with respect both to relatively symmetrical activity between the hemispheres and proportionation of energy along the brain electrical activity frequency spectrum. These embodiments may make use of improved support of closed-loop neurotechnology.

BRIEF DESCRIPTION OF THE FIGURES

The systems, methods, and devices disclosed herein and the following detailed description of certain embodiments thereof may be understood by reference to the following figures. Elements in the figures are presented for illustrative purposes, and they are not necessarily drawn to scale.

DETAILED DESCRIPTION

Figure 1:
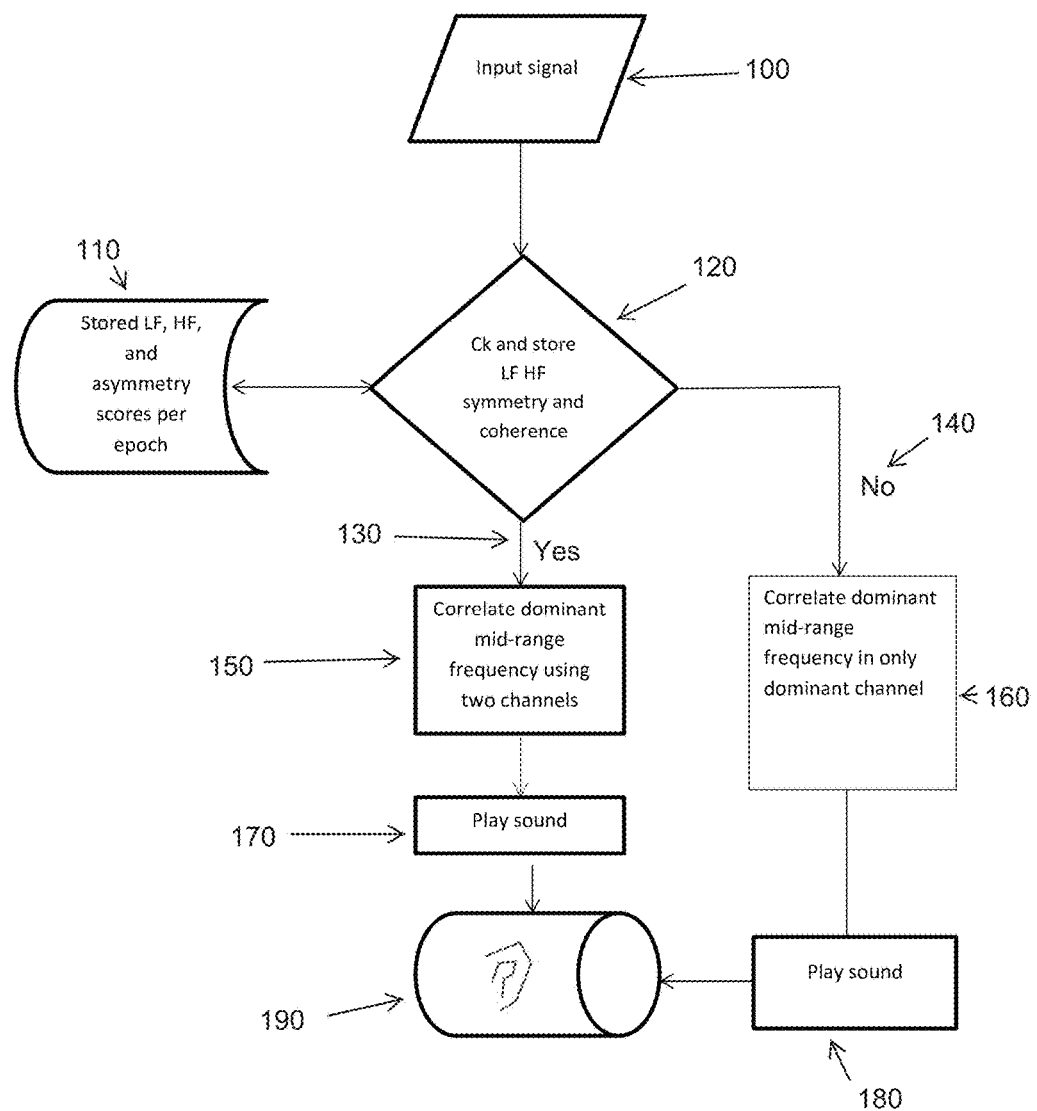
FIG. 1 is a flowchart that depicts steps of rebalancing brain activity according to various methods of the present invention.

The present invention will now be described in detail by describing various illustrative, non-limiting embodiments thereof with reference to the accompanying figures. The invention may, however, be embodied in many different forms and should not be construed as being limited to the illustrative embodiments set forth herein. Rather, the embodiments are provided so that this disclosure will be thorough and will fully convey the concept of the invention to those skilled in the art. Furthermore, headings are provided for the convenience of the reader and are not intended to be and should not be construed as limiting any of the embodiments described herein.

Various embodiments of the present invention provide one or more of devices, systems, and methods for one or more of detecting asymmetries in brain activity, identification of condition states, e.g., stress states and supporting self-balance of brain activity. These embodiments may be used in a user's home or at another location that is convenient for the user.

Measurements of Asymmetry and Identification of Condition States

In one embodiment, the present invention provides a system for measuring asymmetry of brain activity that comprises: (a) a device; (b) an asymmetry determination computer program product; and (c) a central processing unit. Each of these components is described below. The device may be used to identify a condition state and/or to allow the brain to rebalance itself. When used to identify condition states, each condition state may be one that is characterized by or correlated with a profile of observable brain activity, e.g., a stress state or balanced state and any given profile may be correlated with one or more condition states. Each of the components of the system is operable coupled to one or more other components so as to allow each component to performed its intended function.

Devices

The devices are configured to rest on or to be associated with a user's head. A device may, for example, be in the form of a headband, a hat, a visor or a helmet. Optionally, the device contains padding or cushioning over part or all of the surface area that will come in contact with the user's head. In addition to any cushioning that is present, the device may comprise a shell or housing for one or more other elements or pieces of hardware, and the shell may have an outer surface that is rigid, e.g., plastic or soft, e.g., mesh or a combination thereof. In some embodiments, the overall structure of the device is symmetrical between the right and left sides, which may be referred to as right and left halves. The device is considered to be symmetrical between the right half and the left half if the gross morphology is the same between the right half and the left half, regardless of whether there is any small device or structure in only one half, for example, one or more of a transmitter or receiver or computer chip, or there are components on both halves but they are oriented differently, e.g., turned any number of degrees relative to the corresponding component on the other half, and/or they are located a few millimeters away from the exact mirror location of the corresponding component on the other half of the device. In one embodiment, the device is configured as a headband, wherein the headband is in the form of a visor that is designed to stretch from ear-to-ear around and across the forehead of the user when in use.

The device comprises a set of channels, which are the structures that are configured to detect brain activity. The channels may be arranged in pairs of corresponding lobe channels. The phrase "a pair of corresponding lobe channels" refers to two channels that are located on opposite halves of the device, i.e., right and left sides, preferably at or close to mirror image locations of each other and in the same or similar orientations. For illustrative purposes, the device is described as having four channels that are arranged to collect data from two sets of corresponding lobes, e.g., the left frontal lobe, the right frontal lobe, the left temporal lobe and the right temporal lobe. As persons of ordinary skill in the art will recognize, the device could exist with different numbers of channels for each lobe and multiple pairs of channels for different lobes. For example, 1, 2, 3, 4, 5, 6, 7, 8, 9, 10 or more pairs of channels may be present for each lobe. The number of pairs of channels may be different or the same for different corresponding lobes, and the number of sets of corresponding lobes may be two, three or four, e.g., frontal and temporal; frontal and parietal; frontal and occipital; parietal and occipital; parietal and temporal; occipital and temporal; frontal, parietal and occipital; frontal, parietal and temporal; frontal, occipital and temporal; parietal, occipital and temporal; and frontal, parietal, occipital and temporal. As used herein, the phrase "frontal lobe" includes the frontal lobe itself and the frontal pole lobes.

In some embodiments, there may be: (i) a first pair of corresponding lobe channels, wherein the first pair of corresponding lobe channels comprises, consists essentially of or consists of a right first lobe channel and a left first lobe channel, wherein the right first lobe channel and the left first lobe channel are located on opposite halves of the device, and (ii) a second pair of corresponding lobe channels, wherein the second pair of corresponding lobe channels comprises, consists essentially of, or consists of a right second lobe channel and a left second lobe channel, wherein the right second lobe channel and the left second lobe channel are located on opposite halves of the device. Corresponding channels are preferably located at mirror image locations of each other, i.e., equidistant from the center of the device, at the same height along the device and at the same distance from the front of the device. Furthermore, preferably the first lobe and the second lobe are different lobes.

Each channel comprises at least one sensor and is configured to measure electromagnetic energy in a region of a brain of a user. Thus, the sensors can detect changes in electric potential and generate a measurement of electromagnetic energy. The sensors may comprise electrodes and for each channel of data to be read there may be one or more electrodes. The electrode may form or be part of the electronic read device that sits against the skin. Thus, each electrode may be a brain rhythm read device for a particular channel.

Preferably, the channels are configured to measure electromagnetic energy simultaneously. Optionally, in addition to EEG sensors, there are EEG amplifiers. Each channel also comprises one or more circuits to transmit data directly or indirectly through hardware wires and/or circuits and/or wirelessly to a common location on the device. The common location may, for example, be a central location, i.e., at or along a line of symmetry of the device (near the top, the base or in between) or the common location may be at a location that is not central and thus is in only one of the halves of the device (e.g., the right half or the left half).

In some embodiments, the right first lobe channel is positioned to measure electromagnetic energy from the right frontal lobe, the left first lobe channel is positioned to measure electromagnetic energy from the left frontal lobe, the right second lobe channel is positioned to measure electromagnetic energy from the right temporal lobe, and the left second lobe channel is positioned to measure electromagnetic energy from the left temporal lobe. In other embodiments, the right first lobe channel is positioned to measure electromagnetic energy from the right temporal lobe, the left first lobe channel is positioned to measure electromagnetic energy from the left temporal lobe, the right second lobe channel is positioned to measure electromagnetic energy from the right frontal lobe, and the left second lobe channel is positioned to measure electromagnetic energy from the left frontal lobe.

In addition to the pairs of lobe channels, there may be one or a pair of reference sensors. When there is a pair of reference sensors, each sensor may, for example, be positioned within the device so that when the device is in use, there is a reference sensor at or near each of the user's ears. When there is only one reference sensor and the device is in use, it may be located at or near either the left ear or the right ear. In some embodiments, the system is configured such that it can dynamically switch which sensors are used as reference sensors. In these embodiments, one or more channels may be configured to serve as a references sensor and there may or may not be separate references sensors located at or near one or both ears. The dynamic switching may, for example, occur at preprogrammed regular or irregular time intervals.

Optionally, the device further comprises a data storage unit, wherein the data storage unit is configured to store measurements of electromagnetic energy. In some embodiments, the data storage unit is located at or near the common location and is associated with a device processing unit, e.g., a computing device in the form of a chip that is configured to receive information from the channels and to coordinate processing and/or storage of the information. When there is a data storage unit, optionally the device has a USB port and/or a microUSB port and/or an HDMI port that allows for the transfer of data to a thumb drive or other portable data transfer structure that is capable of being inserted into a portal of a computer.

In some embodiments, the device further comprises a transmitter. The transmitter may be located at or near the common location, and it may be capable of wirelessly or through wired connections, transmitting one or more data packages from the device processing unit to a central processing unit. The one or more data packages comprise information that corresponds to the measurement of electromagnetic energy. Each data package may comprise information from a single channel, information from a pair of channels for the same time period(s), or information from a plurality of pairs of channels for the same time periods(s).

In some embodiments, the device is portable and lacks wired connections to the central processing unit. In these embodiments, the device communicates wirelessly with the central processing unit. In other embodiments, the device is portable and is capable of communicating with the central processing unit either wirelessly or through wired connections that are removable. In other embodiments, the device is capable of communicating with the central processing unit only through wired connections.

Asymmetry Determination Computer Program

The asymmetry determination computer program product comprises an algorithm that determines whether the difference in brain activity in corresponding lobes is at an undesirable level. This undesirable level may be referred to herein as a threshold or material difference in energy between the lobes. The asymmetry determination computer program product may be stored in a tangible medium or stored in or accessed through the cloud or a network. When applied, the asymmetry determination computer program product determines whether during one or more time periods there is a threshold difference in energy between: (1) energy measured within any one or more of a first subrange of frequencies, a second subrange of frequencies, and a third subrange of frequencies from a right lobe channel; and (2) energy measured within a corresponding subrange of a corresponding left lobe channel, wherein the second subrange consists of frequencies greater than the frequencies in the first subrange, and the second subrange consists of frequencies smaller than the frequencies in the third subrange. Thus, when there are channels for two sets of corresponding lobes, the computer program product may be configured to compare energies from:

a first subrange of the right first lobe channel to a first subrange of the left first lobe channel;
a second subrange of the right first lobe channel to a second subrange of the left first lobe channel;
a third subrange of the right first lobe channel to a third subrange of the left first lobe channel;
a first subrange of the right second lobe channel to a first subrange of the left second lobe channel;
a second subrange of the right second lobe channel to a second subrange of the left second lobe channel; and
a third subrange of the right second lobe channel to a third subrange of the left second lobe channel;

or it may be configured to compare energies from:

a first subrange of the right first lobe channel to a first subrange of the left first lobe channel;
a third subrange of the right first lobe channel to a third subrange of the left first lobe channel;
a first subrange of the right second lobe channel to a first subrange of the left second lobe channel; and
a third subrange of the right second lobe channel to a third subrange of the left second lobe channel.

The asymmetry determination computer program product is configured to determine whether there is a threshold difference in energy by comparing a calculated energy of the frequencies within each subrange from the right first lobe channel with a calculated energy of the frequencies within each subrange from the left first lobe channel over a plurality of predetermined time periods, and simultaneously comparing a calculated energy of the frequencies within each subrange from the right second lobe channel with a calculated energy of the frequencies within each subrange from the left second lobe channel over a plurality of predetermined time periods. The predetermined time periods may overlap or may be non-overlapping.

In some embodiments, the subranges are divided as follows: the first subrange is frequencies from about 0.005 hertz to about 15 hertz; the second subrange is from about greater than 15 hertz to about 30 hertz and the third subrange is from greater than about 30 hertz to about 48.50 hertz. The aforementioned dividing points are used for illustrative purposes and changes in these points are within the scope of the invention. In another embodiment, the first subrange is from about 0.005 hertz to about 6.5 hertz, the second subrange is from about greater than 6.5 hertz to 16.5 hertz and the third subrange is from about greater than 16.5 hertz to about 48.5 hertz. These ranges are contiguous but, also within the scope of the present invention would be using subranges that are non-contiguous.

In some embodiments, the ranges are determined for each individual by looking for their dominant frequency range, which becomes the second subrange. Thus, the dominant frequency range may be the range when the person is most at rest, e.g., between 0.005 Hz and 36 Hz or between 16 and 23 Hertz. Alternatively, all systems could use either of these as the second subrange for one of both sets of corresponding lobes.

In order to determine whether asymmetries exist, the computer program product may be configured to calculate the energy from each subrange within each of a plurality of predetermined time periods for data from each channel and compare these energies to those measured from the same subrange of the corresponding lobe in the other hemisphere for the same time periods. Thus, one may calculate the average energy in a subrange. In order to do this, one may make use of digital signaling processors and band-pass filters. Additionally, the device may make use of Fast Fourier Transformation protocols to transform signals from time to frequency domains.

In some embodiments, the threshold difference of a subrange between hemispheres of a set of lobes is at least 3%, at least 10%, at least 20%, at least 30%, at least 40%, at least 50%, at least 60%, at least 70%, at least 80%, at least 90%, at least 100%, at least 150% or at least 200% difference in energy over each of at least 5, at least 10, at least 20, at least 30, at least 40, at least 50, at least 60, at least 70, at least 80, or at least 100 consecutive time periods, wherein the time periods are 0.001 to 50 seconds or 5 to 30 seconds in length. In other embodiments, the threshold difference is at least 3%, at least 10%, at least 20%, at least 30%, at least 40%, at least 50%, at least 60%, at least 70%, at least 80%, at least 90%, at least 100%, at least 150% or at least 200% difference in energy over at least 60%, at least 70%, at least 80% or at least 90% of at least 5, at least 10, at least 20, at least 30, at least 40, at least 50, at least 60, at least 70, at least 80, or at least 100 consecutive time periods, wherein the time periods are 0.001 to 50 seconds or 5 to 30 seconds in length.

In one embodiment, the threshold difference between hemispheres of the temporal lobe is 3% or more over each of at least 5%, at least 10%, at least 20%, at least 30%, at least 40%, at least 50%, at least 60%, at least 70%, at least 80%, at least 90% or 100% of at least 5, at least 10, at least 20, at least 30, at least 40, at least 50, at least 60, at least 70, at least 80, or 100 consecutive time periods, wherein the time periods are 0.001 to 50 seconds or 5 to 30 seconds in length. In another embodiment, the threshold difference between hemispheres of the frontal lobe is 3% or more over each of at least 5%, at least 10%, at least 20%, at least 30%, at least 40%, at least 50%, at least 60%, at least 70%, at least 80%, at least 90% or 100% of at least 5, at least 10, at least 20, at least 30, at least 40, at least 50, at least 60, at least 70, at least 80, or at least 100 consecutive time periods, wherein the time periods are 0.001 to 50 seconds or 5 to 30 seconds in length.

In one embodiment, in order to determine if a lobe qualifies for rebalancing, the energy profile of each subrange of each channel is summarized over an epoch, which is a time period between 0.002 and 30 seconds. The most recently processed summaries are stored in a revolving area of computer memory, e.g., the most recent 3-25 are processed and stored or the most recent 5-15 are processed and stored e.g., the most recent 5. These may be stored on one or both of the devices and a remote data storage unit that is within or associated with or in communication with the central processing unit.

As each epoch is stored, the low (first), middle (second), and high (third) subranges of the corresponding channels are compared to each other. These comparisons determine whether the threshold asymmetry has been crossed, and for example, the eligibility of corresponding lobes to initiate or to continue the balancing process or to be the basis for an identification of a condition state.

By way of non-limiting examples, one may design the bounds of a mid-range based on eye-state (open vs. closed), age, or montage scalp placement of sensors or combinations thereof. Additionally, one can look for clusters of hemispheric frequency balances in a resting state for an individual or population and from there one may select a midrange (also referred to as a middle range). In some embodiments, the width of the midrange may be 4-18 hertz or 6-16 hertz or 8-14 hertz or 10-20 hertz. Further, in some embodiments the lower bound of the midrange may, for example, be 3.5 hertz, 4 hertz, 4.5 hertz, 5 hertz, 5.5 hertz, 6 hertz, 6.5 hertz, 7 hertz, 7.5 hertz, 8 hertz, 8.5 hertz, 9 hertz, 9.5 hertz, 10 hertz, 10.5 hertz, 11 hertz, 11.5 hertz, 12 hertz, 15 hertz, 18 hertz or 20 hertz and the upper bound may be 12 hertz, 13 hertz, 14 hertz, 15 hertz, 18 hertz, 20 hertz, 22 hertz, 24 hertz, 26 hertz, 28 hertz, 30 hertz or 32 hertz.

Non-limiting examples of subranges appear in Table 1 below.

TABLE 1

| Example Number | First Subrange (Hz) | Second Subrange (Hz) | Third Subrange (Hz) |
|---|---|---|---|
| 1 | 0.125-10 | 10.1-25 | 25.1-48.50 |
| 2 | 0.125-15 | 15.1-20 | 20.1-48.50 |
| 3 | 1.0-8 | 12-30 | 30.1-45 |
| 4 | 2-12 | 15-19 | 32-40 |
| 5 | 0.125-12.5 | 12.6-22.4 | 22.5-48.50 |
| 6 | 0.125-.3.4 | 3.5-20 | 32.1-48.50 |
| 7 | 2.8 | 8.1-32 | 32.1-37 |

The Central Processing Unit

The central processing is configured to receive the measurements of electromagnetic activity from the device and to execute the asymmetry determination computer program product. The central processing unit may, for example, be located in a computer, which may, for example, be in the form of a tablet, a smart phone, a personal computer, or a networked computer.

In some embodiments, the computer is not connected to the device through any wires. Thus, it is configured to communicate wirelessly with the device. In other embodiments, it is connected to the device through wires. In still other embodiments, the central processing unit may be within the device and its functions are part of the device processing unit. Furthermore, the central processing unit may be configured to execute computer program products automatically upon the receipt of instructions or data that may be used as input for the computer program product. Additionally, in some embodiments, a computer that houses the central processing unit comprises one or more of a graphic user interface, memory in the form of a data storage structure, an input device (e.g., a keyboard and/or mouse), a transmitter for transmitting information, and a receiver for receiving information. In some embodiments, the transmitter and/or receiver may be designed to send and to receive information that is communicated wirelessly through 3G, 4G, or Bluetooth technology or combinations thereof.

The central processing unit is capable of generating a data message, wherein the data message contains information that indicates an observation of a material asymmetry in activity between one or both of: (i) the measurements from one or more subranges of the right first lobe channel and the measurements of corresponding subranges of the left first lobe channel; and (ii) the measurements from one or more subranges of the right second lobe channel and one or more subranges of the measurements from the left second lobe channel.

Methods

The systems described above may be used to measure asymmetry. Methods for detecting asymmetry may begin by measuring brain activity. Through sensors, one may detect changes in electric potentials and then digitize the information. This digitized information is sent to the central processing unit. As noted above, sensors from different sets of corresponding lobes may be monitored at the same time. Consequently, different stress states that are present at the same time may be identified from different subranges of frequencies from different sets of corresponding lobes.

If the threshold level of asymmetry is detected, the data may be used to identify a condition state by activating a computer protocol that accesses a computer file that associates asymmetries in brain activity with one or more condition states. In some embodiments, the set of condition states may comprise, consist essentially or consist of stress. As persons of ordinary skill in the art will recognize, these stress states may correlate with one or more of arousal, hyper-arousal, hypo-arousal, pleasure, confusion, depression, fear, anxiety, risk, maladaptive behavior, or anger.

The methods described herein are preferably automated. Thus, when the device is activated for a purpose, each of the steps necessary for carrying out that purpose occurs in response to the applicable data that is transmitted or received and generates the applicable output and/or initiates the next step in the method.

Mitigation of Asymmetry

In some embodiments, the systems of the present invention may be configured to allow for rebalancing of asymmetry. These systems comprise: (a) a device; (b) an asymmetry determination computer program product; and (c) a central processing unit, as described above and further comprise (a) at least one speaker within the device; (b) a correlation algorithm; and (c) a playback computer program product. Below, each of these features is described in further detail.

Speakers

The at least one speaker is configured to play a variable sequence of acoustical stimuli. In some embodiments the at least one speaker is a set of two speakers, e.g., a left speaker and a right speaker. These speakers may, for example, be located in earbuds or configured as the earpieces of headphones.

In one embodiment the at least one speaker comprises a right speaker and a left speaker and the right speaker is configured to be situated at or near the right ear of the user and the left speaker is configured to be situated at or near the left ear of the user when the device is in use. The set of speakers contains or is operably coupled to elements that contain the requisite hardware and connections in order to receive digital data that corresponds to a variable sequence of acoustical stimuli, and to convert the data into sound to play the variable sequence of acoustical stimuli.

Correlation Algorithm

The correlation algorithm correlates each of a plurality of frequencies from a set of brain wave frequencies with an acoustical stimulus to form a variable sequence of acoustical stimuli. In some embodiments, the correlation algorithm comprises a database and computer code instructions for retrieving information from the database. When the variable sequence of acoustical stimuli is used for rebalancing it may provide a real time mirror of said plurality of dominant frequency brain waves from the second subrange. By way of a non-limiting example, in the database dominant frequencies may be preassigned to sounds such as tone or musical notes or cords. These sounds may be assigned randomly or systematically, e.g., when using musical notes, higher frequencies may be associated with notes that are higher on a scale within the range of human hearing.

A "variable sequence of acoustical stimuli" may be a set of sounds or tones, e.g., musical notes that are played in sequence. In some embodiments, a plurality or each of the sounds has the same duration or different durations and the same or different pitches. In some embodiments, the sounds may, for example, be selected from a scale. As persons of ordinary skill in the art will recognize, a scale is the set of notations that have been accredited by human experience. Thus, in some embodiments, the variable sequences of acoustical stimuli are not based on exact frequencies but instead are based on a relationship between frequencies, or based on the scale of a brain.

The variable sequence of acoustical stimuli is received by the speakers directly or indirectly from the central processing unit. In some embodiments, the variable sequence of acoustical stimuli is received in a plurality of data packets that is played in real time as they are received. As persons of ordinary skill in the art know, "real time" refers to the time that it takes to receive, to process, and to transmit data. For the human experience, this time may be negligible, e.g., milliseconds or shorter or longer. Furthermore, although the present disclosure refers to a sequence of sounds, because they are being generated and played in real time, the playback begins before the complete sequence has been generated.

In some embodiments, the variable sequence of acoustical stimuli is created only after the threshold asymmetry described above is detected. In other embodiments, as soon as a user puts on the device a variable sequence of acoustical stimuli is played to support the balance of whichever corresponding lobe or set of lobes have the greater asymmetry in a subrange, regardless of whether it has crossed a threshold level is used. Alternatively, the method begins with a user selected corresponding set of lobes from which to create the starting variable sequence of acoustical stimuli or a preprogrammed default corresponding set of lobes. In these embodiments, to start, the method looks to the middle range of the applicable lobe(s) and determines the dominant frequencies in each which formulate a basis for selecting the acoustical stimulus for the playback sequence.

Playback Computer Program Product

The playback computer program product is stored in a tangible medium or in the cloud or on a network and is configured: (i) to be activated when there is said material asymmetry in activity between the measurements from a subrange of frequencies of either the right first lobe channel and the left first lobe channel or the right second lobe channel and the left second lobe channel (and in some embodiments to be activated when there is no asymmetry but the device has nonetheless been activated or turned on for use); (ii) to apply an algorithm (e.g., a correlation algorithm) that translates a plurality of dominant frequency brain waves from the second subrange of the lobe for which there is said material asymmetry into acoustical stimuli (and in some embodiments, to look to a dominant frequency of a second subrange even if there is no threshold asymmetry); and (iii) to control playing said acoustical stimuli through said at least one speaker, wherein said acoustical stimuli provide a real time mirror of said plurality of dominant frequency brain waves from the second subrange. The playback computer program product may be stored on the device or at a location other than on the device. The correlation algorithm may be distinct from the playback computer program product, e.g., separate file, or a module located within it or within a computer program product that contains both it and a module for the playback computer program.

As the variable sequence of acoustical stimuli is being played back, each of the pairs of corresponding channels continues to be monitored and to collect data.

When data is collected from a plurality of lobes, then there may be the case that no threshold asymmetry is detected in either or any lobes. In these circumstances, the system may be designed to start with a particular default set of corresponding lobes and at regular intervals switch between sets of corresponding lobes until a threshold difference in energy is detected.

Methods for Restoring Brain Symmetry

In some embodiments, the present invention provides a method for restoring brain symmetry. The method begins with simultaneously measuring electromagnetic activity of a user's brain through a set of channels. As described above, the set of channels may comprise, consist essentially of, or consist of: (i) a right first lobe channel and a left first lobe channel that form a first pair of lobe channels, wherein the right first lobe channel and the left first lobe channel are located on opposite halves of a device, and (ii) a right second lobe channel and a left second lobe channel that form a second pair of lobe channels, wherein the right second lobe channel and the left second lobe channel are located on opposite halves of the device, wherein each channel is configured to measure electromagnetic energy in a region of a brain of a user and to generate a measurement of electromagnetic energy. Preferably, the first pair of lobe channels and the second pair of lobe channels are oriented to measure brain activity from different lobes of the brain. In these embodiments, when referring to halves of the device, the present disclosure means the right half and the left half.

Next, the asymmetry determination computer program product is activated. The asymmetry determination computer program product may be stored locally or on a smartphone, tablet or other computer, or on a network in a tangible medium or exist in a computing cloud. In some embodiments, upon receipt of the measurements of brain activity, it determines whether there is a threshold difference in energy between energies measured within any one or more of a first subrange of frequencies, a second subrange of frequencies, and a third subrange of frequencies of corresponding lobe channels.

Next, when there is a determination of a threshold difference in energy, the method may automatically activate or access a correlation algorithm. The correlation algorithm looks for dominant brain wave frequencies from, e.g., the second subrange. For each of a plurality of frequencies over time from the set of dominant brain wave frequencies from the lobe for which there has been a determination of a threshold difference in energy, the correlation algorithm identifies an acoustical sound, e.g., a musical note. In some embodiments, when an imbalance is detected, the dominant frequency for identifying the sound is formulated or taken from the set of frequencies for the left and right sides of the lobes in which the imbalance was detected. The dominant brain wave frequency may, for example, be the dominant frequency between the subranges of the two lobes for which the threshold asymmetry was detected or an average of the dominant frequency between them. If during mirroring, the imbalance gets worse and it is in the high or low subranges, then the dominant frequency of the middle subrange may be taken exclusively from only one side of the pair of lobes. The imbalance might be due to one side being much greater in amplitude than the other. In these cases, to address worsening imbalances, the methods may be designed to obtain dominant frequencies exclusively from the side that is less or least optimized.

As noted above, in alternative embodiments, the method does not look for asymmetries prior to creating the initial variable sequence of acoustical stimuli. Instead, it looks for the greatest asymmetry regardless of threshold comparison or has a default setting for the lobe from which to begin creating the variable sequence of acoustical stimuli. As the system causes a variable sequence of acoustical stimuli, it continues to monitor all channels, and upon a trigger event, for example a predetermined level or degree of change in asymmetry, is capable of dynamically switching to the middle range of another set of corresponding lobes channels as a source of dominant frequencies from which to generate the variable sequence of acoustical stimuli.

Next, a variable sequence of acoustical stimuli is created by playing or combining each acoustical stimulus. The variable sequence of acoustical stimuli is played through a sound output device such as one or more speakers. The variable sequence of acoustical stimuli is created to address an asymmetry in one set of lobes by playing stimuli that are associated with dominant frequency or frequencies of the middle range from the same set of lobes in which the asymmetry was detected. Thus, by way of a non-limiting example, if in the frontal lobes, an asymmetry is detected in the first subrange that is greater than the threshold level, then the method will automatically look for the dominant frequencies in the middle range of the frontal lobes, activate the correlation algorithm to determine which stimulus corresponds to that frequency and through the playback computer product, cause an output of that stimulus.

As the dominant frequency or frequencies change in the middle range, the stimuli to play will change and the variable sequence of acoustical stimuli will be developed. The variable sequence of acoustical stimuli is developed and played back in near real time. Thus, for convenience of the reader, the variable sequence of acoustical stimuli is described as referring to the complete set of stimuli played back, but playback begins before the complete sequence is created. The variable sequence of acoustical stimuli may be played in both speakers or only in the speaker on one side of the head, e.g., the side for which the frequencies of the asymmetric subrange was larger or on the side for which the frequencies of the asymmetric subrange was smaller.

As the variable sequence of acoustical stimuli is being played back, each of the pairs of corresponding channels continues to be monitored. If the asymmetry is reduced to a subthreshold level or eradicated, the variable sequence of acoustical stimuli may continue until the end of the user's session. In these circumstances, the middle range of the same set of corresponding lobes may be used for the source of the variable sequence of acoustical stimuli until the end of the session; or if asymmetry is detected in the other corresponding set of lobes, the middle range of that set of lobes may be used as the source or the variable sequence of acoustical stimuli; or if no asymmetry is detected in the other corresponding set of lobes, after a predetermined amount of time, the system may nonetheless switch to the other set of lobes as the source of the variable sequence of acoustical stimuli.

When looking to threshold differences in energy, in some embodiments, the threshold difference in energy between energies measured is determined for each of a plurality of epochs, e.g., 5 to 100 or 10 to 50, wherein each epoch ranges from 5 to 30 seconds. Thus, the asymmetry must exist for at least a certain amount of time to be considered actionable.

In some embodiments, the measurements are made at a rate of at least 500 samples per second or at least 1000 samples per second. In some embodiments, 500 to 1000 samples per second are collected.

In some embodiments, the channels are configured to measure frequencies up to about 98.5 hertz.

Additionally, optionally for each epoch, a coherence qualification test for bi-hemisphere acoustical mirroring is performed in each of the regions. Coherence is calculated as the square magnitude of the cross-spectral density of two signals divided by the product of their auto spectral densities at a given frequency.

$$\text{Coherence Function}(f) = \frac{[\text{Magnitude}(\text{Averaged } S_{AB}(f))]^2}{\text{Averaged } S_{AA}(f) \times \text{Averaged } S_{BB}(f)}$$

The result is a coherence value between zero and one for the signals of the two regions. A zero for the coherence value indicates no correlation between the two signals in terms of signal phase and amplitude. A value of one for the coherence indicates an exact match between the two signals (signal phase and amplitude). One method for calculating coherence is based on the MATLAB (matrix laboratory) mscohere function. This involves overlapping segments that are windowed, the resulting windowed values being used to calculate the cross spectrum and power spectra. By way of a non-limiting example, one may use a segment size that is four times the sample rate, a window segment size is the sample rate, a Hamming window, and an overlap is 75%.

Thus, to calculate the coherence, the signals are divided into overlapping segments that are then windowed. Fast Fourier Transforms (FFTs) are performed because cross-spectral and auto spectral densities are frequency domain values. The coherence is determined by averaging the coherence value from each segment. Thus, the asymmetry determination computer program products may be configured to determine whether or one or both of a threshold level of asymmetry and/or a threshold level of lack of coherence exists during rebalancing.

A method of the present invention may be further understood by reference to FIG. 1. An input signal is received from a client 100. Next one checks for asymmetry in the low frequency, mid frequency and high frequency ranges and also during rebalancing, which may begin as soon as the device is used, i.e., the device mirrors the brain without the client required to be taught to do so and checks for coherence, 120. For each epoch, one stores any low frequency and high frequency and asymmetry and coherence scores 110.

If there is both asymmetry and coherence within the tolerance 130, then one correlates the dominant mid-range frequencies per time units using two channels 150 with sounds from the correlation database and plays the sounds 170 through a speaker 190. If there is either asymmetry or coherence (or both) outside of the tolerance range 140 one correlates dominant mid-range frequencies from only one channel 160 and then (after accessing the correlation database) plays the sounds 180 through the speaker 190.

Dynamic Monitoring and Rebalancing

As persons of ordinary skill in the art will recognize the brain is constantly active. Therefore, even if asymmetries are detected in one pair of lobes, the brain may at the same time or at other times, have asymmetry in other lobes.

In some embodiments, a threshold difference is detected between measurements from channels of both the first pair of corresponding lobe channels and the second pair of corresponding lobe channels. In these cases, the dominant brain wave frequencies may be selected from the second subrange of frequencies of the lobes for which a subrange had the greater asymmetry or a user may select which lobe he or she would prefer to balance first and then when balance is below the threshold level, the system may automatically switch to the other lobes.

In some embodiments, the asymmetry is detected from between corresponding subranges of the first lobe, and the dominant frequency from which the variable sequence of acoustical stimuli is generated is from the middle subrange of the first set of corresponding lobes. The method may further comprise continuing to search for asymmetries during playing of the variable sequence of acoustical stimuli, and if greater asymmetry is detected in another set of lobes, e.g., a switching threshold asymmetry in energies is detected from at least one of the corresponding subranges measured from the second corresponding lobes, then the method further comprises creating a new variable sequence of acoustical stimuli, wherein the new variable sequence of acoustical stimuli comprises stimuli for each of a set of dominant frequencies from the second pair of lobes; and playing the new variable sequence of acoustical stimuli. If the asymmetry is from a different subrange of the same corresponding lobes, then one would continue with generating the variable sequence of acoustical stimuli from the dominant frequency of the second or middle subrange of those lobes. In some embodiments, a switching threshold is an asymmetry that is either a threshold asymmetry as described above provided that it is greater than the greatest asymmetry in the other corresponding set of lobes or is at least 3%, at least 5%, at least 10%, at least 20%, at least 40%, at least 60%, or at least 80% greater than the greatest asymmetry in the other corresponding set of lobes.

In some embodiments, the asymmetry is detected from between corresponding subranges of the second corresponding lobes and the dominant frequency from which the variable sequence of acoustical stimuli is generated is also from the second pair of lobes. The method may further comprise continuing to search for asymmetries during playing of the variable sequence of acoustical stimuli, and if greater asymmetry is detected in another lobe, e.g., a switching threshold asymmetry in energies is detected from at least one of the corresponding subranges measured from the first pair of lobes, then the method further comprises creating a new variable sequence of acoustical stimuli, wherein the new variable sequence of acoustical stimuli comprises an acoustical stimulus for each of a set of dominant frequencies from the first lobes; and playing the new variable sequence of acoustical stimuli.

In some embodiments, one may simultaneously analyze coherence in each of the frequency ranges of two, three, or four corresponding sets of lobes of the brain, and if there is insufficient coherence in any pair of lobes, these may be triaged in order of degree of lack of coherence and addressed in that order. When addressing a lack of coherence one may, e.g., redefine the middle subrange to generate a different variable sequence of acoustical stimuli.

Dynamic rebalancing may occur after there has been a trigger event. A trigger event may be a predetermined increase in a difference in energy between energies measured within any one or more of a first subrange of frequencies, a second subrange of frequencies, and a third subrange of frequencies of corresponding lobe channels from which either the dominant frequency was measured or the dominant frequency was not measured. Alternatively or additionally, the trigger event is a predetermined decrease in a difference in energy between energies measured within any one or more of a first subrange of frequencies, a second subrange of frequencies, and a third subrange of frequencies of corresponding lobe channels from which either the dominant frequency was measured or the dominant frequency was not measured. The predetermined increase or decrease may be an absolute number or a percentage, e.g., at least 2%, at least 5%, at least 10%, at least 20% or at least 30%.

Hardware

Figures 2A, 2B:
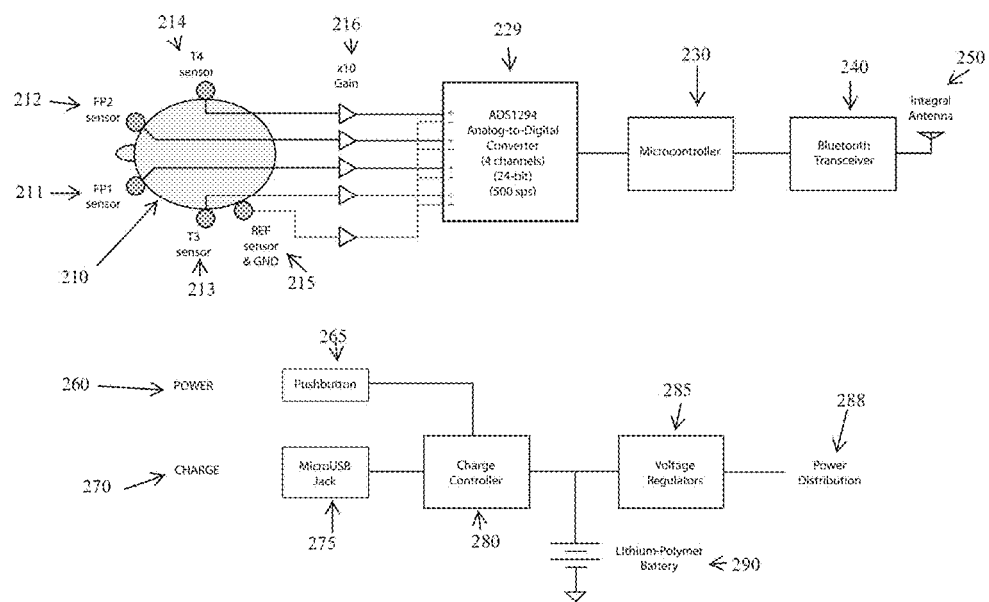
FIGS. 2A and 2B illustrate an example of hardware configuration that may be used in connection with the present invention.

In some embodiments, the devices of the present invention contain all of the electronics for acquiring data, including sensors (which may be wet or dry), a Bluetooth wireless data link to a phone or tablet, a rechargeable battery, and a microUSB jack for charging between uses. An example of a configuration of the hardware that may be used on or in connection with a device is illustrated by reference to FIGS. 2A and 2B.

Electrical Design

The system's ADC (Analog-to-Digital-Converter) 229 (which is an amplifier) on a device 210 of the present invention may, for example, be an ADS1294 chip from Texas Instruments. Four channels of data are simultaneously-acquired at a 500-sample-per-second rate, providing a frequency spectrum resolvable up to almost 250 Hz. In a 24-bit ADC, there is a theoretical amplitude resolution of 145 dB (decibels). This new BST system yields over 120 dB dynamic range with ADC inputs shorted, and typically over 90 dB dynamic range with-respect-to the sensor inputs. The result is an EEG system that: (i) needs no adjustable gain ranging amplifiers; (ii) has vast headroom that allows power line(s) and other common-mode signals to coexist (and subsequently be removed from the desired differential signal) without signal clipping issues, and a very low noise floor. As persons of ordinary skill in the art know, a noise floor is how far down a signal can be read without being washed out by noise. Clipping is flattening of a signal above/below an upper range for the positive/negative amplitude of a signal where nothing is read due to potential harmonic noise interference and/or manifestations of lack of clear signal information above the upper+/−amplitude limit.

Information collected by the four sensor channels (with reference to the reference channel on the ear sensor 215) 211 (FP1 sensor), 212 (FP2 sensor), 213 (T3 sensor) and 214 (T4 sensor) are digitized in a headset and transmitted to the phone/tablet over a wireless Bluetooth link 240. The ear sensor is a standard reference. As persons of ordinary skill in the art are aware, electrical potential is determined as it exists as a difference between two points. The active sensors have a standard reference (the ear), which is approximately zero and generally also has the same interference as the active sensors. Therefore, Actual potential=(Active−Reference)

for each separate active sensor and the interference recorded in both the active and the reference sensors then cancel each other out. The ear sensor is depicted as the reference point, but in other embodiments, one may use a dynamic reference in order to find the difference between any two points.

The scalp sensors use active FET buffers with Schottky diodes to clamp transient events such as static discharge, and use a "balanced-driver" from each scalp sensor. This balanced-driver inverts each sensor signal to provide a differential cable drive as is typically used, for example, on balanced microphone and other pro-audio applications.

An EEG system is comprised of a number of sensors that are placed at specific locations on the scalp. A "reference" sensor is typically clipped onto an earlobe, which is an electrically-quiet location on the head. The signals of interest are measured differentially: sensor with-respect-to reference. The signals of interest are in the microvolt-to-millivolt range, but they are summed with larger "common-mode" signals that exist in unison on the reference and sensor signals. The differential measurement removes most of the common-mode signal, however, the sensor amplifier inputs have a maximum allowed common-mode range, which is only a few volts. If this range is exceeded, the desired signals cannot be measured.

The human body acts as an antenna capacitively-coupled to Earth ground, and immersed in the electromagnetic fields of surrounding AC power lines and other noise sources. The largest contribution is from the 50-Hz or 60-Hz power system. The body will have a certain potential with respect to Earth ground, and the EEG amplifier system, which is also capacitively-coupled to Earth ground, will likely have a different potential with respect to Earth ground. When the amplifier sensors are connected to the body, the difference between the body and amplifier potentials (due to capacitive coupling of each) results in potentials of 50-Hz or 60-Hz and other noise being added as common-mode signals to the reference and sensor amplifier inputs, which is generally in levels far in excess of the amplifier's allowable common-mode range.

An additional EEG system connection to the body is a "ground" electrode, which is utilized to minimize these large common-mode signals. Ground is the point of zero potential in the amplifier circuitry, and when connected to the body, shorts-out the body and amplifier capacitive-coupling paths to Earth ground, thereby eliminating much of the common mode signal. The ground connection may be located at any convenient point on the body.

Lead-Off Detection

In various embodiments, one may use an ear-clip that has a reference sensor on one side of the clip, and a ground connection on the opposite side of the clip. Either ear may be utilized.

To detect a "lead-off" condition, one may utilize a test frequency that is to be applied to the ground electrode at a low amplitude. Each of the sensors are digitized (with-respect-to the reference sensor) by an analog-to-digital converter. This results in a time-domain data stream for each sensor channel. The time-domain data is converted to frequency-domain data by a Fast Fourier Transform, and once the frequency-domain data is obtained, the system monitors the amplitude of the test frequency. This test signal needs to be above the band of interest so as not to affect the normal operation of the system. Because power line frequencies at 50-Hz or 60-Hz may have harmonics at 100-Hz or 120-Hz, in some embodiments, it is preferable to use a test frequency of above 100 Hz that is not a harmonic of 50-Hz or 60-Hz. However, in some instances, power line noise itself (either 50 Hz or 60 Hz depending on the country in which the device is being used) can be measured before powerline filters are applied to the input signal of each channel when the device is first turned on. The levels of the power line noise can then be monitored to determine if the noise levels are relative to each other and then, after the device session has begun, to determine if the noise level of each channel remains consistent to the relative measure of it to the noise level of each of the other sensors. Should noise levels of any channel(s) be extremely differentiated, for example differentiated at an unacceptable level, from the other channels of the device at the time, then a lead-off indication is noted to the user.

There are two gains associated with the differential sensor-to-reference measurement: the actual differential signal gain and the common-mode gain. By nature of the differential measurement, the common-mode signal is minimized, but there is still a small component. The common-mode gain is increased as the series impedance of the two sensors (signal and reference) differ in magnitude. For example, if both sensors have an effective 5,000-ohm series impedance, or both have an effective 50,000-ohm series impedance, the common-mode gain is much the same. However, if one sensor is about 5,000-ohms and the other about 50,000-ohms, then the common-mode gain increases substantially. One consequence of this is the increasing amplitude of power line components.

This common-mode gain will be exploited to detect a lead-off condition. The test frequency applied to the ground electrode will appear as a common-mode signal to all sensors. If the sensors are all making good contact with the scalp, their effective series impedances will be reasonably low. The reference sensor on the ear-clip should also be making good contact. When the system measures the amplitude of the test frequency, it should be rather low as well (on the order of 40-dB or more down). When one of the scalp sensors starts to make poorer contact, the amplitude of the test frequency will increase, rising to a maximum when the sensor is completely off of the scalp.

By selecting an appropriate amplitude for the test frequency applied to the ground electrode, and selecting a trigger threshold (perhaps −20 dB), the system can determine electrode status. If all sensors have a test frequency amplitude below the threshold, then they should all be making acceptable contact, and operation is normal. If one of the sensors has a test frequency amplitude above the threshold, a fault condition, the system can alert the user or practitioner to check and correct the sensor contact. If all of the sensors show a fault condition, then the system can alert that the reference sensor on the ear-clip is likely needing to be checked and corrected.

In various embodiments, the sensors contain differential driver circuitry that is configured to transmit differential signals. A "differential" (a.k.a. "balanced") signal is one that, instead of sending the signal with-respect-to (WRT) a fixed ground, sends both the signal and the inverted signal down a pair of wires (which may, for example, be a twisted-pair of conductors or parallel conductors). This design allows a "common-mode" signal to ride on both wires of the signal pair and substantially be reduced by the differential receiving circuitry, before analog-to-digital conversion. The differential sensor drive not only minimizes common-mode pickup (power line and other ambient signals), but also reduces inter-channel crosstalk. Sensor differential driver circuitry also provides a pre-amplification gain of a factor of ten, 216.

The sensors of the device interconnect via a flexible-circuit to one small electronics module on the left-rear section of the headset, and a second electronics module on the right-rear section. This forms one continuous custom flex circuit, with sensor circuitry directly integrated. The right-rear electronics module provides power to the system through voltage regulators 285, containing a lithium-polymer battery 290, a microUSB jack 275 and charging electronics, and a minimal microcontroller 280 to monitor a power 260 pushbutton 265 and charging state, 270. As a safety precaution, the system may be configured not to operate during charge 280.

The left-rear electronics module contains sensor differential receiving circuitry, band-limiting inputs, the ADS1294 ADC chip, a microcontroller, and a Bluetooth wireless transceiver circuit. The microcontroller, e.g., a 32-bit ARM variant, manages commands sent from the phone/tablet, acquisition of data from the ADS1294 chip, and the streaming of digitized sensor data to the phone/tablet over the wireless link. The system may use a pre-built Bluetooth module, or embedded Bluetooth circuitry directly on the main circuit board, and transmission may occur through an integral antenna 250.

The system may incorporate a user awareness of headset connectivity to the scalp delivered via spoken instructions. This is advantageous because the user is invited to close his or her eyes during use. In this design, there is a hardware/software combination that provides individual sensor impedance testing and delivers results back to the user via spoken instructions, should the impedance on a sensor indicate poor connectivity. The system may also be configured to monitor regularly the connection state of each scalp sensor, and to alert the individual using the audio system that a sensor may not be making adequate contact with the skin. This provides the individual with an opportunity to correct the situation by pressing on the device at the sensor location, or removing and re-installing the device on the head or changing the appropriate sensor insert. Impedance testing ensures that the data being acquired by the system is of a quality level consistent with the goal of providing a quality brain monitoring and circadian regulation function.

Custom Mechanical Design

In some embodiments, the device's physical form factor may be a custom design similar to an eyeglass frame, and it may use injection-molded technology for its production. Ergonomic engineering considerations as appropriate materials of construction may be used as well. In some embodiments, the primary section of the device is formed from a thermoplastic or thermosetting polymer, and optionally, there may be sections formed from an elastomer or conductive elastomer. The custom device design provides not only encapsulation of the flexible circuitry connectivity and miniaturized electronic components, but also a unit that is attractive and comfortable to wear.

Allostatic Neuro-Education

Various embodiments of the present invention may be used in connection with groundwork for allostatic neuro-education ("GANE"). Allostasis refers to stability through change, and the GANE perspective views learners in terms of their neurodevelopment trajectories. Its objective is to support authentic freedom, mediated by competent, integrated, and expansive executive functionality. Its strategy calls for being attuned to rhythms in various forms so as to enable experiential excitement for learning.

In some embodiments, a student uses a device or system of the present invention according to a method of the present invention at least 2, e.g., 2 to 28 or 3 to 21 or 3 to 15 or 2-6 or 3-5 times per week for at least 2, e.g., 3-6 or 4-5 weeks. In some embodiments, the sessions are from 45 minutes to 2 hours in duration. In some embodiments, the student uses a device (or system) and method of the present invention at least 9 times, at least 12 times or at least 15 times. In some embodiments, the usage is from 6 to 60 minutes one or more times per day. In some embodiments, the usage is at least twenty hours over a five week period. As a result of this usage, one may see an educational improvement and thus improve the student's ability to learn. This improvement may include one or more of an increase in I.Q. testing scores or other testing scores, an increase in an ability to maintain attention, and a decrease in undesirable emotional states.

EXAMPLES

Example 1: Allostatic Neuro-Education No. 1

An 18 year-old male carrying a diagnosis of Asperger's syndrome and ADHD (attention-deficit hyperactivity disorder) was exposed to allostatic neurotechnology according to the methods of the present invention. The technology rapidly updated the brain about its own oscillatory activity through the medium of sound.

Prior to participation, the student had been reported as being on edge, hyper-focused and a light sleeper. He had been taking lisdexamfetamine dimesylate (Vyvanse®) 30 mg daily, but tapered off of it prior to participating in the study. He was on the following supplements: astaxanthin, omega 3, blue-green algae, calcium, magnesium and Co-Q 10.

The student participated in fourteen sessions that range from 64-84 minutes long, with a median of 76 minutes. The sessions were spread out over 40 days.

In a follow-up session that took place twelve days after completion of the fourteenth session, the student reported that he felt better, and one of his parent's reported that his teachers noted that his concentration and focus were better in class, and that he had a greater willingness to participate. Further, there was an improvement in his ISI (Insomnia Severity Index), BAI (Beck Anxiety Index), BDI-II (Beck Depression Idex-II) and AQ (Autism Spectrum Quotient) scores, which reflected improvement in sleep reduction and depressive symptoms. Thus, adjunctive use of allostatic neurotechnology was associated with self-adjustments in cognitive systems (attention), arousal (sleep) and social affiliation (class participation). Further details of this example appear on pages 10-13 of Gerdes, Lee et al., *A Groundwork for Allostatic Neuro-education*, August 2015 Vol. 6, pp. 1-13, which is herein incorporated by reference in its entirety.

Example 2: Allostatic Neuro-Education No. 2

A 9 year-old female student with a learning disability related to reading was enrolled in a special education program. Her medical and behavioral health history included enuresis and seasonal allergies. She did not take any medications. Using the same allostatic neurotechnology that was used in Example 1, the student participated in fourteen sessions.

The mother reported the following benefits: a greater degree of calm, being "not so wound up," and being more open. Additionally, within nine months after the initial sessions, the student demonstrated both a faster speed for processing information and a decrease in enuresis.

The next year the student participated in five additional sessions. By the end of the following year, the student's mother reported that she demonstrated significant improvements in reading comprehension. By the year after that, the student's capabilities were at a level that she did not require a special education program. Consequently, she participated in regular eighth grade classes. Thus, the use of allostatic neurotechnology was associated with improvement in emotional well-being, better performance in school and relief from enuresis. Further details of this example appear on pages 13-14 of Gerdes, Lee et al., *A Groundwork for Allostatic Neuro-education*, August 2015 Vol. 6, pp. 1-13, which is herein incorporated by reference in its entirety.

Various aspects of the present invention have been described for use in connection with one or more embodiments. However, unless explicitly stated or otherwise apparent from context, each feature described above in any one embodiment may be used in connection with any and all embodiments.

Example 3: Headband A

Figure 3A:
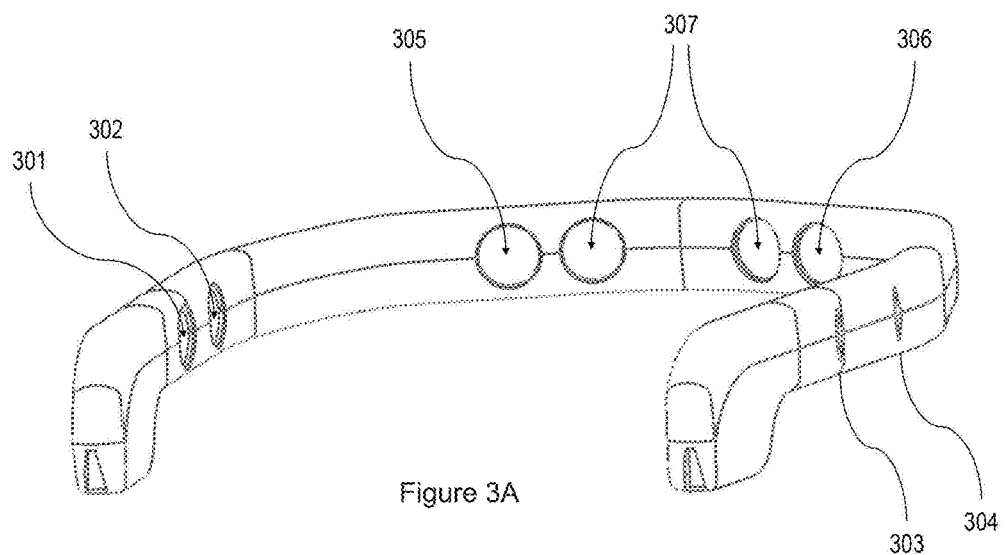
FIGS. 3A and 3B illustrate headbands according to various embodiments of the present invention.

An example of a head-mounted frame is shown in FIG. 3A. The T3 temporal electrodes at 301 and 302 are connected in parallel, providing fit for various head sizes by using a conductive insert in one electrode snap, and a non-conductive insert in the other snap. The T4 temporal electrodes at 303 and 304 are also connected in parallel. Small heads will have the conductive T3 and T4 inserts located at the front-most positions, and large heads will have the conductive inserts located at the rear-most positions. The FP1 frontal electrode is located at 305, and the FP2 frontal electrode at 306. Two ground electrodes are provided at 307. A unique reference scheme is employed in this design: T3 is the reference signal for both FP1 and FP2 channels, and FP1 is the reference signal for both T3 and T4 channels. This design eliminates the need for a separate reference sensor.

Example 4: Headband B

Figure 3B:
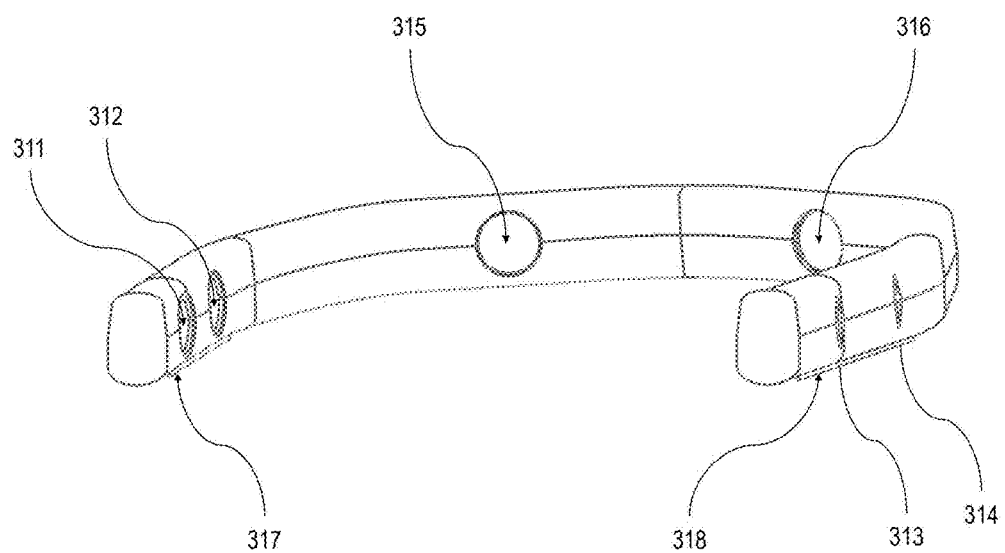

An alternate embodiment of the head-mounted frame is shown in FIG. 3B. The frame is shorter at the rear ends to allow more clearance. Conductive rubber strips are added on the lower part of the frame at 317 and 318 to contact the tops of the ears. The T3 temporal electrodes at 311 and 312, the T4 temporal electrodes at 313 and 314, the FP1 frontal electrode at 315, and the FP2 frontal electrode at 316, are located in the same positions as the first embodiment. The ground electrodes have been removed from the front of the frame, allowing better forehead contact to the FP1 and FP2 electrodes. The ground connection is now located at 317, the conductive rubber strip contacting the top of the left ear. A primary electrical change in this embodiment is the addition of an independent reference connection at 318, the conductive rubber strip contacting the top of the right ear. Each of the four channels, FP1, FP2, T3, and T4, are differential measurements with respect to the reference channel, to minimize common-mode signals.

Example 5: More than Three Subranges

In some embodiments of the comparison of subranges between left and right corresponding lobes, the measuring of electromagnetic energy of each sensor is charted into 11 subranges. Comparison between ranges of corresponding lobes indicates the degree of symmetry of that corresponding lobe and range. The greatest asymmetry is then indicated in real time and is used to indicate the range or ranges used as the range for mirroring the brain based on the dominant frequency in the middle range or ranges indicated. For example the middle range may be designated in subrange "7," if the greatest asymmetry is in the lower frequency subranges, but may be designated in subrange "2 thru 3" if the greatest asymmetry is in an upper frequency range.

Thus, after determining the subrange with the greatest asymmetry, one could look to another predetermined subrange (e.g., 4, 5, 6, 7, or 8), or groupings of subranges (e.g., 5-7 or 4-8) for the dominant frequencies for the source of input for the correlation with sounds that will be played when establishing rebalance.

Examples of subranges divisional into groupings of the eleven subranges are provided in Table 2.

TABLE 2

| Example | Subrange in Hz | | | | | | | | | | |
|---|---|---|---|---|---|---|---|---|---|---|---|
| | 1 | 2 | 3 | 4 | 5 | 6 | 7 | 8 | 9 | 10 | 11 |
| 1 | 0.1-0.5 | .5-2 | 2-4 | 4-8 | 8-16 | 16-24 | 24-30 | 30-34 | 34-38 | 38-44 | 44-98 |
| 2 | 0.2-0.8 | .8-2 | 2-5 | 5-10 | 10-15 | 15-20 | 20-25 | 25-30 | 30-36 | 36-46 | 36-96 |
| 3 | 0.4-1.2 | 1.2-3 | 3-6 | 6-12 | 12-18 | 18-24 | 24-30 | 30-35 | 35-40 | 40-45 | 45-95 |
| 4 | 0.5-1.5 | 1.5-3 | 3-7 | 7-12 | 12-18 | 18-25 | 25-32 | 32-39 | 39-46 | 46-49 | 49-99 |
| 5 | 0.8-1.8 | 1.8-4 | 4-10 | 10-16 | 16-24 | 24-30 | 30-36 | 36-42 | 42-48 | 48-62 | 62-98 |
| 6 | 0.9-2 | 2-4 | 4-7 | 7-11 | 11-16 | 16-22 | 22-28 | 28-35 | 35-43 | 43-52 | 52-92 |

What is claimed is:

1. A method for restoring brain symmetry comprising:
   (a) simultaneously measuring electromagnetic activity of a user's brain through a set of channels, wherein the set of channels comprises
      (i) a first pair of corresponding lobe channels, comprised of a right first lobe channel and a left first lobe channel, wherein the right first lobe channel and the left first lobe channel are located on opposite halves of a device, and
      (ii) a second pair of corresponding lobe channels, comprised of a right second lobe channel and a left second lobe channel, wherein the right second lobe channel and the left second lobe channel are located on opposite halves of the device,
      wherein each channel is configured to measure electromagnetic energy in a region of a brain of a user and to generate a measurement of electromagnetic energy and wherein the first pair of corresponding lobe channels is configured to measure electromagnetic energy from a first lobe and the second pair of corresponding lobe channels is configured to measure electromagnetic energy from a second lobe, wherein the first lobe is not the same as the second lobe;
   (b) activating an asymmetry determination computer program product, wherein the asymmetry determination computer program product is stored in a tangible medium and when applied determines whether there is a threshold difference in energy between energies measured within any one or more of a first subrange of frequencies, a second subrange of frequencies, and a third subrange of frequencies as measured between each channel of each pair of corresponding lobe channels,
   (c) when there is a determination of a threshold difference in energy, activating a correlation algorithm, wherein for each of a plurality of frequencies from a set of dominant middle range brain wave frequencies from the lobe for which there has been a determination of a threshold difference in energy, the correlation algorithm identifies an acoustical stimulus, wherein each of the plurality of frequencies is from the second subrange of frequencies for the lobe for which there has been a determination of a threshold difference in energy;
   (d) creating a variable sequence of acoustical stimuli by combining each acoustical stimulus identified in (c); and
   (e) playing said variable sequence of acoustical stimuli through a sound output device, wherein the set of channels and the sound output device are housed in the device, wherein the device is configured to rest on a user's head and wherein during step (e) said channels continue to measure electromagnetic activity and the asymmetry determination computer program product is further configured to dynamically switch the lobes from which the asymmetry determination computer program product obtains the dominant frequencies upon occurrence of a trigger event.

2. The method according to claim 1, wherein the threshold difference in energy between energies measured is determined for each of a plurality of epochs, wherein each epoch ranges from 5 to 30 seconds.

3. The method according to claim 2, wherein said measurements are made at a rate of at least 500 samples per second.

4. The method according to claim 3, wherein the channels are configured to measure frequencies up to about 100 hertz.

5. The method according to claim 3, wherein the asymmetry determination computer program product is configured to determine whether there is a threshold difference in energy by comparing a calculated energy of the frequencies within each subrange from the right first lobe channels with a calculated energy of the frequencies of the subrange from the left first lobe channels over a plurality of predetermined time periods.

6. The method according to claim 1, wherein the frequencies within the second subrange of frequencies are greater than the frequencies within the first subrange of frequencies and the frequencies within the second subrange of frequencies are smaller than the frequencies within the first subrange of frequencies.

7. The method according to claim 1, wherein if during step (b) a threshold difference is detected and the difference increases, the dominant brain wave frequency is obtained only from the side of the lobe that is least optimized.

8. The method according to claim 1, wherein the trigger event is a predetermined increase in a difference in energy between energies measured within any one or more of a first subrange of frequencies, a second subrange of frequencies, and a third subrange of frequencies of corresponding lobe channels from which either the dominant frequency was measured or the dominant frequency was not measured.

9. The method according to claim 1, wherein the trigger event is a predetermined decrease in a difference in energy between energies measured within any one or more of a first subrange of frequencies, a second subrange of frequencies, and a third subrange of frequencies of corresponding lobe channels from which either the dominant frequency was measured or the dominant frequency was not measured.

10. A system for restoring symmetry in a brain comprising:
   (a) a device, wherein the device is configured to rest on a user's head and said device comprises a set of channels, wherein the set of channels comprises
      (i) a first pair of corresponding lobe channels, wherein the first pair of corresponding lobe channels comprises a right first lobe channel and a left first lobe channel, wherein the right first lobe channel and the left first lobe channel are located on opposite halves of the device, and
      (ii) a second pair of corresponding lobe channels, wherein the second pair of corresponding lobe channels comprises a right second lobe channel and a left second lobe channel, wherein the right second lobe channel and the left second lobe channel are located on opposite halves of the device,
      wherein each channel comprises at least one sensor and is configured to measure electromagnetic energy in a region of a brain of a user and to generate a measurement of electromagnetic energy, wherein the channels are configured to measure said electromagnetic energy simultaneously and the first pair of corresponding lobe channels is configured to measure electromagnetic energy from a first lobe and the second pair of corresponding lobe channels is configured to measure electromagnetic energy from a second lobe, wherein the first lobe is not the same as the second lobe;
   (b) an asymmetry determination computer program product, wherein the asymmetry determination computer program product is stored in a tangible medium and when applied determines whether during one or more time periods there is a threshold difference in energy between energy measured within any one or more of a first subrange of frequencies, a second subrange of frequencies, and a third subrange of frequencies from a right lobe channel and within a corresponding subrange of a corresponding left lobe channel, wherein the second subrange consists of frequencies greater than the frequencies in the first subrange and the second subrange consists of frequencies smaller than the frequencies in the third subrange;
   (c) a central processing unit, wherein the central processing is configured to receive said measurements of electromagnetic activity from the device and to execute the asymmetry determination computer program product;
   (d) a transmitter, wherein the transmitter is capable of wirelessly transmitting one or more data packages to the central processing unit, wherein each of the one or more data packages comprises information that corresponds to the measurement of electromagnetic energy, and the central processing unit is capable of generating a data message wherein the data message contains information that indicates an observation of a material asymmetry in activity between one or both of
      (i) the measurements from a subrange of the right first lobe channel and the measurements of a corresponding subrange of the left first lobe channel; and
      (ii) the measurements from a subrange of the right second lobe channel and the measurements of a corresponding subrange of the left second lobe channel,
   wherein the device further comprises at least one speaker and the system further comprises:
   (e) a correlation algorithm, wherein the correlation algorithm correlates each of a plurality of frequencies from a set of brain wave frequencies with an acoustical stimulus; and
   (f) a playback computer program product, wherein the playback computer program product is stored in a tangible medium and is configured such that
      (i) (a) when there is said material asymmetry in activity between the measurements from a subrange of frequencies of either the right first lobe channel and the left first lobe channel or the right second lobe channel and the left second lobe channel, said computer program product translates a plurality of dominant frequency brain waves from the second subrange of the lobes for which there is said material asymmetry into acoustical stimuli; and (b) where there is no material asymmetry in activity between the measurements from a subrange of frequencies of either the right first lobe channel and the left first lobe channel or the right second lobe channel and the left second lobe channel, said computer program product translates a plurality of dominant frequency brain waves from the second subrange of either the first set of lobes channels or the second set of lobes channels into acoustical stimuli, and
      (ii) said playback computer program product controls playing said acoustical stimuli through said at least one speaker, wherein said acoustical stimuli provide a real time mirror of said plurality of dominant frequency brain waves from the second subrange, and
   wherein the asymmetry determination computer program product is further configured to dynamically switch the lobes from which the asymmetry determination computer program product obtains the dominant frequencies upon occurrence of a trigger event.

11. The system of claim 10, wherein the at least one speaker comprises a right speaker and a left speaker and the right speaker is configured to be situated at or near the right ear of the user and the left speaker is configured to be situated at or near the left ear of the user when the device is in use.

12. The system of claim 11, wherein the right first lobe channel is positioned to measure electromagnetic energy from the right frontal lobe, the left first lobe channel is positioned to measure electromagnetic energy from the left frontal lobe, the right second lobe channel is positioned to measure electromagnetic energy from the right temporal lobe, and the left second lobe channel is positioned to measure electromagnetic energy from the left temporal lobe.

13. The system of claim 12 further comprising a reference sensor.

14. The system of claim 13, wherein the system is configured to process data up to at least 1000 samples per second.

15. The system of claim 14, wherein the system is configured to deliver energy along an outer surface of each sensor and to measure impedance.

16. The system of claim 10, wherein the trigger event is a predetermined increase in a difference in energy between energies measured within any one or more of a first subrange of frequencies, a second subrange of frequencies, and a third subrange of frequencies.

17. The system of claim 10, wherein the trigger event is a predetermined decrease in a difference in energy between energies measured within any one or more of a first subrange of frequencies, a second subrange of frequencies, and a third subrange of frequencies.

18. A method of improving a user's ability to learn, wherein said method comprises applying the method of claim 1 for at least 20 hours over a five week period.

* * * * *